US007045364B2

(12) United States Patent
Limoges et al.

(10) Patent No.: US 7,045,364 B2
(45) Date of Patent: May 16, 2006

(54) ELECTROCHEMICAL IMMUNOASSAYS USING COLLOIDAL METAL MARKERS

(75) Inventors: Benoît Limoges, Gerzat (FR); Laurent Authier, Aubiere (FR); Murielle Dequaire, Clermont Ferrand (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 104 days.

(21) Appl. No.: 10/311,854

(22) PCT Filed: Jun. 25, 2001

(86) PCT No.: PCT/FR01/02000

§ 371 (c)(1),
(2), (4) Date: Jun. 5, 2003

(87) PCT Pub. No.: WO02/01178

PCT Pub. Date: Jan. 3, 2002

(65) Prior Publication Data

US 2003/0186274 A1    Oct. 2, 2003

(30) Foreign Application Priority Data

Jun. 26, 2000    (FR) .................................. 00 08145

(51) Int. Cl.
*G01N 33/553*    (2006.01)
(52) U.S. Cl. .................... 436/525; 423/22; 423/38; 423/522; 436/518; 438/1; 438/104
(58) Field of Classification Search .............. 423/22, 423/38, 522; 436/525, 518; 438/1, 104
See application file for complete search history.

(56) References Cited

U.S. PATENT DOCUMENTS

| 4,313,734 | A |   | 2/1982  | Leuvering |
| 4,853,335 | A |   | 8/1989  | Olsen et al. |
| 5,304,359 | A | * | 4/1994  | Duyvesteyn et al. .......... 423/22 |
| 5,591,581 | A | * | 1/1997  | Massey et al. ................. 435/6 |
| 5,637,508 | A |   | 6/1997  | Kidwell et al. |
| 5,650,333 | A | * | 7/1997  | Holtlund et al. ............ 436/525 |
| 5,851,777 | A |   | 12/1998 | Hunter et al. |

FOREIGN PATENT DOCUMENTS

| EP | 0 258 963 A2 | 3/1988 |
| EP | 0 310 872 A1 | 4/1989 |
| WO | WO 97/04313 A1 | 2/1997 |
| WO | WO 99/32662 A1 | 7/1999 |

OTHER PUBLICATIONS

Alarnes-Varela et al., "Determination of Gold by Anodic Stripping Voltammetry with Carbon Fiber Ultramicroelectrodes", Electroanalysis, 1997, vol. 9, No. 16, pp. 1262-1266.

(Continued)

*Primary Examiner*—Long V. Le
*Assistant Examiner*—Pensee T. Do
(74) *Attorney, Agent, or Firm*—Buchanan Ingersoll, P.C.

(57) ABSTRACT

The invention concerns a method for detecting or quantifying a biological substance coupled with a colloidal metal particle by electrochemical detection, characterised in that it comprises a step which consists in dissolving by chemical treatment of said colloidal metal particle, prior to detection.

15 Claims, 7 Drawing Sheets

OTHER PUBLICATIONS

Authier et al., "Gold Nanoparticle-Based Quantitative Electrochemical Detection of Amplified Human Cytomegalovirus DNA Using Disposable Microband Electrodes", Analytical Chemistry, 2001, vol. 73, No. 18, pp. 4450-4456.

Bagel et al., "Subfemtomolar Determination of Alkaline Phosphatase at a Disposable Screen-Printed Electrode Modified with a Perfluorosulfonated Ionomer Film", Analytical Chemistry, 1997, vol. 69, No. 22, pp. 4688-4694.

Beesley, "Colloidal Gold: A New Revolution in Marking Cytochemistry", Proceedings RMS, 1995, vol. 20, No. 4, pp. 187-196.

Dequaire et al., "An Electrochemical Metalloimmunoassay Based on a Colloidal Gold Label", Analytical Chemistry, 2000, vol. 72, No. 22, pp. 5521-5528.

Frens, "Controlled Nucleation for the Regulation of the Particle Size in Monodisperse Gold Suspensions", Nature Physical Science, 1973, vol. 241, pp. 20-22.

Garcia et al., "Colloidal Gold as an Electrochemical Label of Streptavidin-Biotin Interaction", Biosensors & Bioelectronics, 2000, vol. 15, No. 5-6, pp. 315-321.

Garcia et al., "Adsorptive Stripping Voltammetric Behaviour of Collodial Gold and Immunogold on Carbon Paste Electrode", Bioelectrochemistry and Bioenergetics, 1995, vol. 38, pp. 389-395.

Kalcher, "Chemically Modified Carbon Paste Electrodes in Voltammetric Analysis", Electroanalysis, 1990, vol. 7, pp. 419-433.

Kalcher et al., "Sensors Based on Carbon Paste in Electrochemical Analysis: A Review with Particular Emphasis on the Period 1990-1993", Electroanalysis, 1995, vol. 7, pp. 5-22.

Leuvering et al., "Sol Particle Immunoassay", J. of Immunoassay, 1980, vol. 1, No. 1, pp. 71-91.

McCarthy et al., "The Mechanism of the Oxidative Dissolution of Colloidal Gold in Cyanide Media", J. of Electrochem. Soc., 1998, vol. 145, No. 2, pp. 408-414.

Murray et al., "Synthesis and Characterization of Nearly Monodisperse CdE (E=S, Se, Te) Semiconductor Nanocrystallites", J. Am. Chem. Soc, 1993, vol. 115, pp. 8706-8715.

Olivier, "Conjugation of Colloidal Gold to Proteins", Methods in Molecular Biology, 1999, vol. 115, pp. 331-334.

Storhoff et al., "One-Pot Colorimetric Differentiation of Polynucleotides with Single Base Imperfections Using Gold Nanoparticle Probes", J. Am. Chem. Soc., 1998, vol. 120, pp., 1959-1964.

Tu et al., "Ultrasensitive Heterogeneous Immunoassay using Photothermal Deflection Spectroscopy", Anal. Chem., 1993, vol. 65, pp. 3631-3635.

Ugo et al., "Ion-Exchange Voltammetry at Polymer-Coated Electrodes: Principles and Analytical Prospects", Electroanalysis, 1995, vol. 7, No. 12, pp. 1105-1113.

Van den Berg, "Potentials and Potentialities of Cathodic Stripping Voltammetry of Trace Elements in Natural Waters", Analytica. Chimica. Acta, vol. 250, pp. 265-276.

Wang et al., "Nanometer-Sized Semiconductor Clusters: Materials Synthesis, Quantum Size Effects, and Photophysical Properties", J. Phys. Chem., 1991, vol. 95, pp. 525-532.

Wang et al., "Screen-Printed Ultramicroelectrode Arrays for On-Site Stripping Measurements of Trace Metals", J. of Electroanalytical Chemistry, 1993, vol. 361, pp. 77-83.

Wang et al., "Stripping Voltammetry at Microdisk Composite Electrode Assembly", Electroanalysis, 1995, vol. 7, No. 10, pp. 958-961.

Weller, "Colloidal Semiconductor Q-Particles: Chemistry in the Transition Region Between Solid State and Molecules", Angew Chem. Int. Ed Engl., 1993, vol. 32, pp. 41-43.

Wong et al., "Anodic Stripping Voltammetry at Mercury Films Deposited on Ultrasmall Carbon-Ring Electrodes", Anal. Chem., 1990, vol. 62, pp. 2697-2702.

Yuan et al., "A New Tetradentate β-Diketonate-Europium Chelate that can be Covalently Bound to Proteins for Time-Resolved Fluoroimmunoassay", Anal. Chem., 1998, vol. 70, No. 3, pp. 596-601.

French Search Report corresponding to FR 00/08145 issued on May 10, 2001, 4 pages.

International Search Report corresponding to PCT FR 01/02000 issued on Aug. 12, 2002, 4 pages.

\* cited by examiner

ELECTROCHEMICAL IMMUNOASSAYS USING COLLOIDAL METAL MARKERS

This application is a 371 of PCT/FR01/02000 filed on Jun. 25, 2001.

The detection and quantification of biological substances using immunoassay methods or methods for assaying DNA fragments by nucleic acid hybridization are extremely important in many fields of clinical biology (medical and biological research, diagnosis, genetics, screening for illicit substances in trace amounts, etc.) or even in the environmental field (detection of contaminants such as pesticides or bacteria). These methods make it possible to satisfy the double criteria of selectivity and sensitivity. Among these methods, immunoanalysis with a marker, based on antigen/antibody affinity recognition, is particularly effective and has become widespread due to the development of a large range of nonradioactive markers such as enzymatic, fluorescent or chemiluminescent markers, generally coupled to spectroscopic detection. However, each marker has its own advantages and disadvantages. Specifically, an ideal marker should satisfy various requirements; it should:

1) be detectable in a sensitive manner using analytical instruments which are inexpensive and easy to manipulate,
2) allow the labeled molecule (tracer) to remain soluble and stable in the assaying media,
3) allow simple and effective labeling at a reasonable cost,
4) having a long lifetime,
5) be of no risk to the individual handling it,
6) produce a tracer having a reactivity close to the unlabeled molecule,
7) produce a minimal background noise.

Among the markers which have been marketed, fluorescent and luminescent markers, developed at the beginning of the 1970s, have many advantages: they are generally nontoxic and stable, and detection thereof is very sensitive. However, they require relatively sophisticated and expensive equipment, and the measurement is often affected by endogenous fluorescence associated with sample matrix effects.

Enzymatic markers, which appeared at the same time as fluorescent markers, are probably today the most popular due to their notable catalytic properties, but also because of their ability to trigger, for certain substrates, colored reactions which permit the use of a very simple detector, such as a calorimeter, or even a manipulator's eye. Enzymatic markers are the basis for methods called ELISA (Enzyme-Linked ImmunoSorbant Assay). These too have their own disadvantages however. Certain substances present in the sample may inhibit the enzyme. In addition, they are relatively fragile and have a limited lifetime. Moreover, the background noise can be considerable.

Metal-based markers were introduced toward the end of the 1970s, with the aim, partly, of remedying certain of the abovementioned disadvantages. Metal-based markers are distinguished according to their chemical nature, namely colloidal metal particles, metal ions, coordination complexes, organometallics or else metalloproteins. Depending on their nature, various analytical techniques can be associated with them, such as time-resolved fluorescence, atomic absorption spectrophotometry or Fourier transform infrared, or else electrochemical techniques such as polarography or voltammetry.

Compared to spectrophotometric methods, electrochemical techniques have many advantages: the measurements can be made in very small volumes of liquid (less than a microliter), in medium which is possibly turbid (in the case of sera), with the possibility of offering a good sensitivity for inexpensive, possibly portable (small in size) equipment. Although electrochemical techniques make it possible to detect organometallic markers or ionic metals down to nanomolar ($10^{-9}$ M) concentrations, this often remains insufficient, however, compared to fluorescent markers which themselves can be detected down to picomolar ($10^{-12}$ M) thresholds. The electrochemical detection strategy developed in the present invention shows that it is possible to attain concentrations of a metallic marker of the order of $10^{-12}$ M.

The invention relates more precisely to a method for electrochemical detection of a colloidal metal particle used as a marker in an immunoassay. The invention also relates to the quantitative or qualitative determination of compounds which may be haptens, antigens or antibodies, but also compounds such as DNA or RNA fragments. In general, the invention may be extended to all analytical methods involving a specific, affinity interaction between a ligand and a host molecule, and in which it is necessary to add a marker for substantially quantifying said interaction. Furthermore, many formats of immunoassays, whether competitive or noncompetitive, or of methods of nucleic acid hybridization, preferably in heterogeneous phase, can be applied.

The use of colloidal metal particles as a marker is not new. Specifically, they are used very commonly as a contrasting agent in electromicroscopy techniques, in particular in the form of gold colloids coupled to antibodies for the purpose, for example, of determining the distribution of an antigen at the surface of a cell (Beesley, *Proceedings RMS*, 1985, 20, 187–196). On the other hand, the use of a colloidal metal particle as a marker in the context of an affinity assay is relatively uncommon. In this respect, the existence of a patent (U.S. Pat. No. 4,313,734) and of a publication (Leuvering et al., *J. Immunoassay*, 1980, 1, 71–91) relating the use of a marker based on colloidal gold or colloidal silver in the context of an immunoassay with detection by atomic absorption or colorimetry may be noted. Other quite similar patents also relate the use of gold colloid as markers in immunoassays with calorimetric detection (U.S. Pat. No. 4,853,335, EP0310872, EP0258963). A detection, also calorimetric, has recently been described for the analysis of DNA fragments by hybridization, via a colloidal gold marker (Storhoff et al., *J. Am. Chem. Soc.* 1998, 120, 1959–1964).

As regards electrochemical detection, a method for immunoanalyzing or assaying DNA by hybridization, involving the electrochemical detection or quantification of a colloidal metal marker, does not, for the moment, appear to have been described. The existence of an article concerning the direct detection of a gold colloid covered with antibodies and adsorbed to the surface of a carbon paste electrode can, however, be reported (Gonzalez-Garcia and Costa-Garcia, *Bioelectrochem. Bioenerg.* 1995, 38, 389–395). However, application to an immunoassay, although envisioned, was not demonstrated.

In order to test this hypothesis, the inventors sought to verify whether or not it was possible to carry out an immunoassay as envisioned by the authors, i.e. an immunoassay taking place at the very surface of the electrode and for which, after immunoreaction, the colloidal gold marker which has reacted in the proximity of the surface of the electrode is directly detected. The result of this experiment made it possible to conclude that it was not possible to detect the gold colloid in this way, probably because the latter is no longer in immediate contact with the surface of the electrode. The present invention makes it possible to be free of this problem by virtue of an indirect detection of the colloidal metal marker, which by the same token allows the use of a solid phase which may be different from the surface of the electrode.

Thus, the present invention allows the detection or quantification of a biological substance coupled to a colloidal metal particle, by electrochemical detection, said colloidal metal particle being dissolved, and detected by electrochemistry after having been reprecipitated at the surface of the electrode. This makes it possible to increase the local concentration and the sensitivity threshold. The subject of the invention is therefore a method for detection or quantification of a biological substance coupled to a colloidal metal particle, by electrochemical detection, characterized in that it comprises a step of dissolving said colloidal metal particle.

The electrochemical immunoassay method developed in the present invention can not only be more sensitive than the current enzymatic immunoassay techniques, but also offer the possibility of determining and/or quantifying several compounds simultaneously if several colloidal metal markers which are different in nature are used. Specifically, electrochemical methods permit the simultaneous detection of several metals in the course of the same measurement. In addition, colloidal metal markers offer the advantage of being much more stable than radioisotopic or enzymatic markers, and they permit simple labeling of many substances, at low cost, without any loss of activity of these substances.

The chemical treatment to dissolve the colloidal metal particle is carried out in an acidic medium containing an oxidant. The concentration of oxidant is chosen so as to be in sufficient excess to dissolve the highest concentrations of colloidal metal marker. A solution of hydrobromic acid containing bromine ($Br_2$) or hypobromous acid (HBrO) or a mixture of the two as oxidant is preferred (for example: $10^{-4}$ M of $Br_2$ in 0.1 or 1 M HBr), in particular when dissolution of a gold colloid is desired. A solution of hydrochloric acid (for example 0.1 M) containing a bromide salt (concentration $\geq 0.1$ M) and bromine may also be suitable. Depending on the nature of the metal colloid to be dissolved, other acidic media for dissolution ($H_2SO_4$, $HClO_4$, HF, etc.) and oxidizing reagents ($I_2$, $Cl_2$, HClO, HIO, $H_2O_2$, $HNO_3$, $CN^-$, $Cr_2O_4^-$, $MnO_4^-$, ...) may be envisioned.

After dissolution, an additional treatment may be necessary to remove the excess oxidizing reagent such as bromine. To do this, an excess of phenol, aniline, hydrazine, oxine or one of their derivatives, or else preferably an excess of 3-phenoxyacetic acid, may be added to the medium. The latter is preferable since it is less toxic. A concentration of $5 \times 10^{-4}$ M is generally sufficient. The bromine may also be removed by degassing.

It may be advantageous to add in solution a reagent capable of complexing the metal ion in order to promote detection thereof. Indeed, complexation can transform a nonelectroactive metal ion into a detectable electroactive compound. In addition, the complexed metal ion, because it has a more marked hydrophobic nature, can adsorb to the electrode and thus be more detected with more sensitively by adsorptive cathodic stripping voltammetry (van den Berg, *Anal. Chim. Acta*, 1991, 250, 265–276).

After the metal has dissolved, it is reduced at the surface of the electrode, preferably by applying a very negative potential. The potential is then varied in order to reoxidize the metal, which then goes into solution. The intensity of the voltammetric peak (surface) reflects the amount of metal deposited on the electrode, and therefore the amount of colloidal particles initially present in the solution. This therefore makes it possible to perform the assaying. When particles consisting of different metals are used, simultaneous detection is possible due to the distinct reoxidation potentials of the various metals.

Thus, it is possible to deduce the presence and/or the amount of biological substance initially coupled to the colloidal particle, as a function of the presence and/or amount of metal electrodeposited at the surface of the electrode.

The colloidal metal particles may consist of metal, such as gold, silver, copper, platinum, rhodium, palladium, iridium, nickel or iron colloids, or else of metal compounds, such as, for example, metal oxides or halides or chalcogenides, such as $Ag_2O$, AgI, $Bi_2O_5$, $Cd_3P_2$, CdS, CdSe, CdTe, $Co_2O_3$, $CrO_3$, $Cu_2S$, $HgI_2$, $MnO_2$, PbS, $PbO_2$, $SnO_2$, $TiO_2$, $RuO_2$, ZnO, ZnS or $ZnO_2$, or metal hydroxides. In general, any metal or metal compound which can be detected electrochemically can be envisioned, preferably transition metals (van den Berg, *Anal. Chim. Acta*, 1991, 250, 265–276). Practical requirements mean that preference is given to the use of metals or metal compounds which are only barely present, or not at all, in the assaying medium, and more particularly those which offer the best detection limits with respect to the electrochemical techniques used. The invention has been demonstrated in particular for a gold colloid.

The metal-based colloidal particles can be obtained using one of the many methods described in the scientific literature (Hayat, Ed, *Colloidal gold: principles, methods, and applications*; Academic Press: San Diego, Calif., 1991—Mackay and Texter, Eds, *Electrochemistry in colloids and dispersions*, VCH Publishers: New York, 1992—Murray et al., *J. Am. Chem. Soc.* 1993, 115, 8706–8715—Frens, *Nat. Phys. Sci.* 1973, 241, 20–22—U.S. Pat. No. 5,637,508—Weller, *Angew. Chem. Int. Ed. Engl.* 1993, 32, 41–43—Wang and Herron, *J. Phys. Chem.* 1991, 95, 525–532). Depending on the method of production, the particles may be between 1 and 200 nm in size, with a very low dispersion. In the present invention, metal colloids between 5 and 100 nm are preferred. The use of a particle of considerable size is liable to improve the sensitivity of the assay.

Depending on the format and the type of assay, the colloidal metal particle can be coupled to an antibody, a protein receptor, an antigen, a hapten, a protein, a peptide, an oligonucleotide or a nucleic acid fragment (in particular DNA or RNA). The term "coupling" is intended to mean any method of chemical or physical attachment, direct or indirect, to the surface of the particle, such as a covalent bond or an adsorption via electrostatic interactions, hydrogen bridges, etc. Many coupling protocols have been described (Beesley, *Proceedings RMS*, 1985, 20, 187–196—Oliver, *Methods in molecular biology*, 1999, 115, 331–334). The species then labeled with the metal particle is then used as a reagent which, in combination with immunochemical reagents based on antibodies, protein receptors, haptens, antigens, proteins, peptides, oligonucleotides, or DNA or RNA fragments, buffer solutions, other chemical reagents, and an electrode-based electrochemical detection system, will make it possible to assay a given substance.

The principle of the invention is, by way of example, illustrated in FIG. 1, in the case of a sandwich-type non-competitive immunoassay (FIG. 1A), and also for a competitive immunoassay (FIG. 1B).

For the first approach (FIG. 1A), the compound to be determined (the analyte) is initially captured with a first ligand (in the present case an antibody; for a hybridization assay, this would be an oligonucleotide) immobilized on a solid phase. The solid phase for immobilizing the ligand may, for example, be the bottom of a microcuvette (in the case of FIG. 1), the surface of a microbead (optionally magnetic), the surface of a membrane or else the surface of the electrode. After a given incubation period, optionally followed by a washing step, a second ligand (here an antibody) labeled with a metal colloid is added in such a way that it reacts with the analyte previously extracted on the solid phase. The solid phase thus constituted is then washed then treated with an appropriate volume of a solution of reagent able to dissolve the colloidal metal marker which has reacted with the solid phase. Then, the metal thus solubilized in the ionic state is detected and quantified using an electrode either immersed in the solution (in situ method—FIG. 1A), or after transfer of the solution (ex situ method). The electrochemical response can then be qualitatively or quantitatively linked to the substance to be assayed.

In the case of the second approach (FIG. 1B), the method consists in bringing a sample containing the substance to be assayed into contact with a known amount of said substance labeled with a metal colloid, and a certain amount of ligand (antibody) immobilized on a solid phase and directed against this substance. After a given reaction time, the nature and the amount of metal colloid present in the fraction bound is then, after an optional washing step, determined as indicated above after dissolution and then electrochemical detection.

The use of a solid phase consisting of microbeads, for example made of latex or else of ferromagnetic oxide, may be particularly advantageous for improving the sensitivity and lowering the limit of detection. Specifically, the microbeads can be concentrated, after the immunoreaction step, on a small surface, such as, for example, the surface of a filtering membrane (U.S. Pat. No. 4,853,335—Tu et al., *Anal. Chem.* 1993, 65, 3631–3665) or else the bottom of a conical tube, thus offering the possibility of dissolving the metal colloid in a smaller volume of liquid than that in which the immunoreaction took place.

Methods based on agglutination and/or precipitation in homogeneous phase of the colloidal metal marker in the course of an immunoreaction or oligonucleotide hybridization can also be envisioned (U.S. Pat. No. 5,851,777). In this case, the aggregates formed are isolated and then dissolved and detected as previously.

As regards the nature of the electrodes, carbon-based electrodes are preferred, and more particularly disk electrodes (FIG. 2A) and strip microelectrodes (FIG. 2B) obtained by screen-printing with a carbon-based ink. These electrodes are in fact particularly well suited since they can be mass-produced at low cost, and can therefore optionally be for single use. In addition, their geometric form and also their size can be readily modifiable. However, other types of electrode may be used, such as electrodes made of glass carbon, graphite, composite materials containing carbon, carbon fibers, and/or carbon paste. In addition, the surface of the electrodes can be treated electrochemically or chemically in order to improve the sensitivity of detection of the dissolved metal (Kalcher, *Electroanalysis*, 1990, 2, 419–433—Kalcher et al., *Electroanalysis*, 1995, 7, 5–22— Ugo and Moretto, *Electroanalysis*, 1995, 7, 1105–1113). This may be, by way of example, modification of the surface of the electrode or of the composition of the ink, with a polymer capable of attracting metal ions via electrostatic interaction or complexation, or else electrochemical pre-treatment of the surface of the electrode. Depositing a mercury film may also prove to be advantageous for certain metal ions which are difficult to detect on a carbon electrode.

As regards the method of producing the electrodes, the screen-printing technique is preferable, although other methods of industrial production, such as rotogravure, inkjet printing, or optionally photolithography may be adapted.

According to the characteristics of the invention, the use of microelectrodes, preferably of strip microelectrodes, obtained by screen-printing is particularly advantageous since they offer the possibility of carrying out measurements in very small volumes (of the order of a few microliters) for analytical performances which, in terms of sensitivity and limit of detection of metal ion, are generally improved (Wong and Ewing, *Anal. Chem.* 1990, 62, 2697–2702— Wang et al., *J. Electroanal. Chem.*, 1993, 361, 77–83— Wang and Armalis, *Electroanalysis*, 1995, 7, 958–961— Alames-Varela and Costa-Garcia, *Electroanalysis*, 1997, 9, 1262–1266).

FIG. 3, which compares the calibration curves (current densities) of $AuBr_4^-$ in 0.1 M HBr, obtained on a screen-printed strip microelectrode with a surface area $S=1.7\times10^{-4}$ cm$^2$ (curve 1) and on a screen-printed disk macroelectrode with a surface area $S=0.0962$ cm$^2$ (curve 2), confirms better sensitivity in the case of the strip microelectrode. These curves were obtained by linear anodic stripping voltammetry in the following way: (I) electrodeposition of gold at a constant potential of $E=-0.3$ V for 300 s, (ii) then linear potential scan from 0.2 V up to 1.1 V at a rate of 50 mVs$^{-1}$. The peak current ($i_p$) appears around 1.0 V, linked to oxidation of the gold, and is taken as the analytical response.

It in fact appears that the use of microelectrodes makes it possible to obtain deposition of the metal which is more effective than with a macroelectrode. Specifically, the use of macroelectrodes requires the solution to be agitated in order to ensure that a sufficient amount of metal deposits at the surface of the electrode. Surprisingly, the inventors have observed that the use of microelectrodes makes it possible to do without this agitation step. This may explain the gain in sensitivity observed, although other hypotheses, due to the very nature of the microelectrode (very small in size), may also be envisioned.

Various techniques of electrochemical analysis may be used to assay the dissolved metal ions. They are preferentially anodic stripping voltammetry (or polarography) with a potential scan which may be linear, cyclic, square-ware, normal pulse or differential pulse, or with a superimposed sinusoidal voltage, or else anodic stripping chronopotentiometry. However, other techniques may be used, such as ion exchange voltammetry, adsorptive cathodic stripping voltammetry (or polarography) with a scan which may be linear, cyclic, square-ware, normal pulse or differential pulse, or with a superimposed sinusoidal voltage, or else chronoamperometry, chronocoulometry or linear, cyclic, square-wave, normal pulse or differential pulse voltammetry (or polarography) or voltammetry (or polarography) with a superimposed sinusoidal voltage. These techniques require a possibly two-electrode or even three-electrode assembly, i.e. an assembly comprising the abovementioned measuring electrode, a reference electrode and, optionally, an auxiliary electrode. In order to avoid contamination of the assaying medium with the metal or the electrolyte of the reference electrode, it is advantageous to isolate this electrode with an extension which consists, at its end, of a porous material, and which is filled with an electrolyte. A reference electrode screen-printed using an ink based on silver and silver chloride may also be envisioned. Here again, it may be useful to isolate this electrode via an electrolyte bridge, such as, for example, an ionic conducting gel or an ionic conducting polymer, in order to avoid interference from the silver ions during a measurement.

The invention also relates to a kit for assaying at least one biological compound. According to the characteristics of the invention, this kit comprises at least one reagent labeled with a colloidal metal particle and at least one electrode. The kit according to the invention may also contain at least one reagent for dissolving the colloidal metal particle and, optionally, a reagent for eliminating the excess oxidizing reagent. The kit may also contain a reagent capable of complexing the metal ion, in order to promote detection thereof. Finally, the kit may also contain instructions in order to enable the method according to the present invention to be carried out.

The following examples illustrate the characteristics of the invention, but should not be considered to limit the invention.

EXAMPLES

Example 1

Detection of Streptavidin Labeled with a Gold Colloid After Specific Attachment to the Bottom of a Microwell The experiments are carried out at ambient temperature.

The bovine serum albumin (BSA, fraction V), the biotin-amidocaproyl coupled to BSA (B-BSA, biotin content: 8–12 mol/mol of BSA), the streptavidin labeled with colloidal gold (S—Au) 20 nm in diameter, and also the streptavidin coupled to albumin onto which 10 nm colloidal gold particles are adsorbed (SA-Au) come from Sigma Chemical Co.

Figure 4:
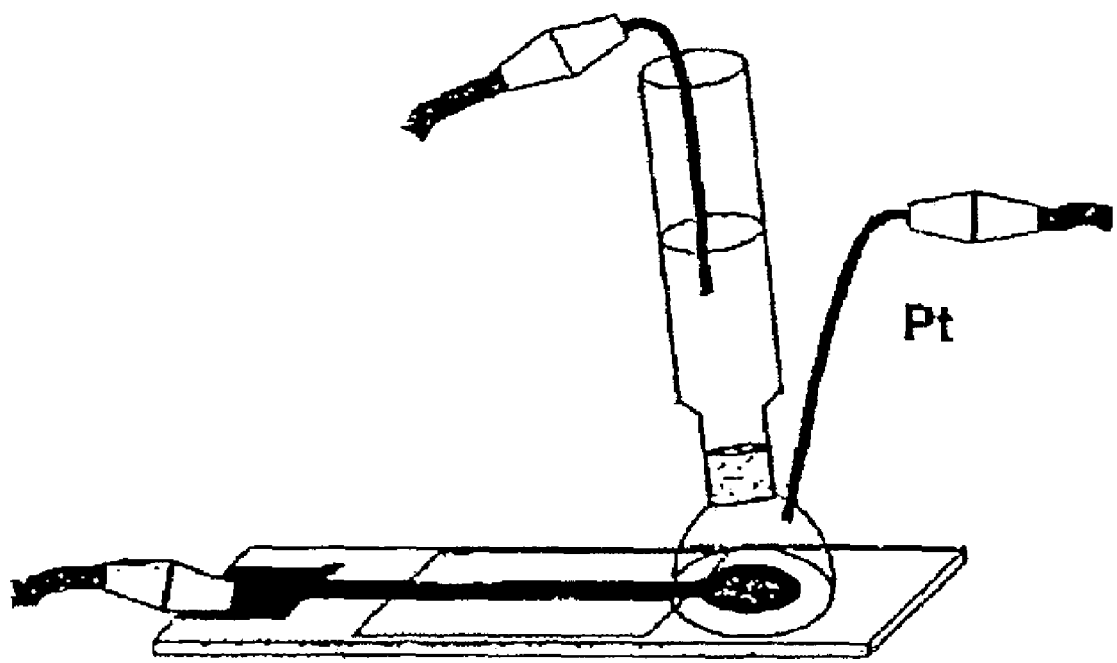
FIG. 4. Diagrammatic representation of the measuring device used to detect the gold dissolved in a small volume of a drop of solution.

100 µl of B-BSA at 10 µg ml$^{-1}$ in a bicarbonate buffer (15 mM $Na_2CO_3$; pH 9.6) are pipetted at the bottom of a polystyrene microwell (Nunc) an allowed to incubate for 2 hours. After having emptied the microwell and rinsed it with 110 µl of phosphate buffer (PBS: 4.3 mM $NaH_2PO_4$, 15.1 mM $Na_2HPO_4$ and 50 mM NaCl; pH 7.4), 100 µl of PBS containing 0.1% of BSA (PBS-BSA) are added and allowed to incubate for 2 hours. The microwell is then emptied and rinsed 3 times with 110 µl of pure water. Next, 35 µl of a solution of S—Au or SA-Au at x µg.ml$^{-1}$ (0.003<x<3) in a PBS-BSA buffer containing 0.05% of Tween 20 (PBS-BSA-T) are then introduced into the microwell and allowed to react for 3 hours. Once emptied, the microwell is thoroughly washed with 3×110 µl of PBS-BSA-T, and then with 2×110 µl of PBS. The gold colloid attached to the walls of the microwell is then dissolved by introducing 40 µl of a solution of $Br_2$ at a concentration of $10^{-4}$ M in 1 M HBr. After 5 minutes, a volume of 35 µl is removed from the microwell and transferred onto the surface of a screen-printed carbon disk electrode (S=0.0962 cm$^2$, electrode prepared according to the method described in the ref.: Bagel et al., *Anal. Chem.* 1997, 69, 4688–4694), to which are added 5 µl of a fresh solution of 3-phenoxypropionic acid at 4×10$^{-3}$ M in 1 M HBr. A reference electrode (Ag/AgBr, NaBr$_{sat}$) extended via an extension containing a saturated solution of NaBr, and an auxiliary electrode are them immersed in the 40 µl of solution previously deposited onto the surface of the screen-printed carbon electrode, as shown by the diagram in FIG. 4. The linear anodic stripping voltammetry measurements are then carried out in the following way:

1) electrodeposition of the gold at a constant potential of E=−0.3 V for 300 s, 2) then a linear potential scan from 0.2 V up to 1.1 V at a rate of 50 mVs$^{-1}$.

Figure 5:
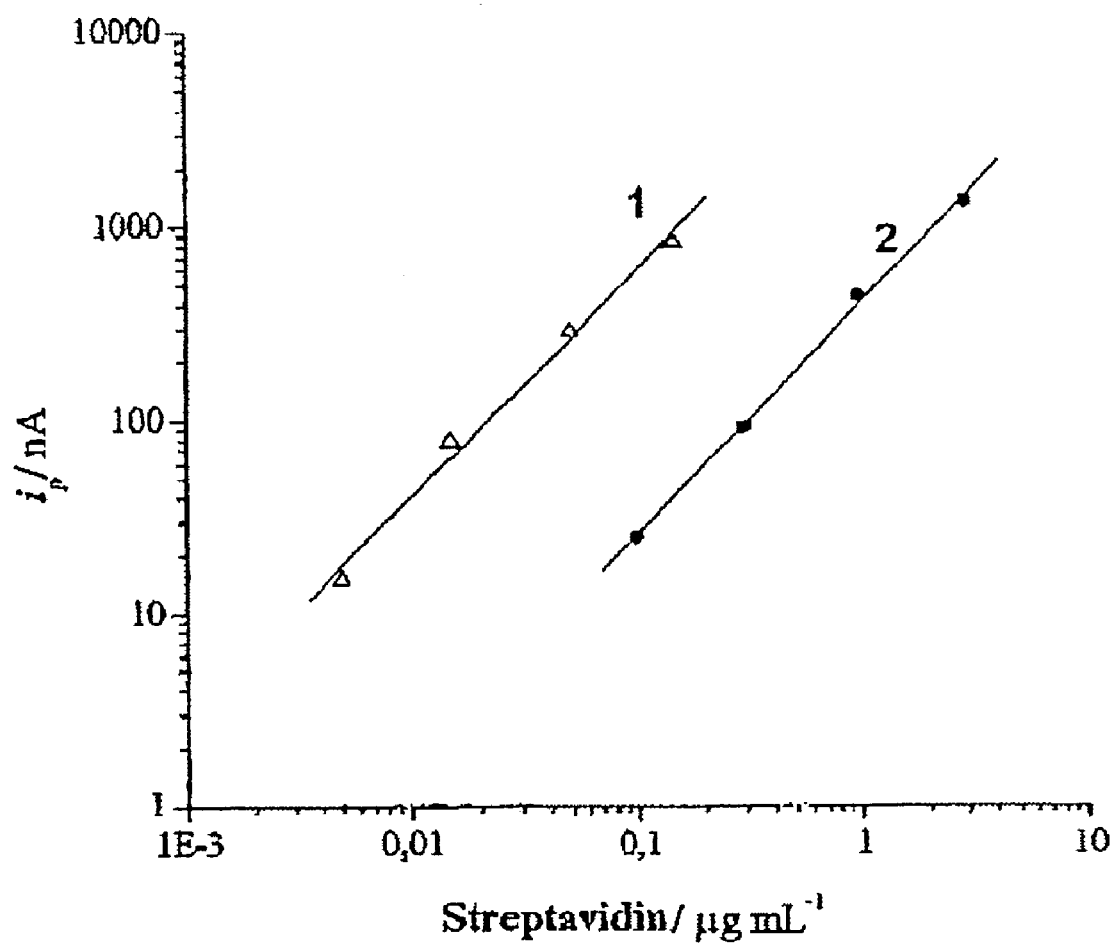
FIG. 5. Calibration curves for two colloids of gold covered with streptavidin.

The peak current ($i_p$) which appears around 1.0 V, linked to oxidation of the gold, is taken as the analytical response. The measurement may also be the integral of the peak, which then corresponds to a coulomb quantity ($Q_p$). The calibration curves are represented in FIG. 5, on a logarithmic scale, for each of the streptavidins labeled with gold. Better sensitivity with the SA-Au (curve 1) than with the S—Au (curve 2) can be noted.

Example 2

"Sandwich" Immunoassay for an Immunoglobulin

The ovalbumin (OA, grade III) and the goat immunoglobulin G (IgG) is marketed by Sigma Chemical Co. The anti-goat IgG labeled with an 18 nm gold colloid, and also the unlabeled anti-goat IgG, are polyclonal antibodies from the Jackson Immunoresearch Laboratories.

60 µl of a solution of anti-IgG at 24 µg ml$^{-1}$ in a PBS buffer are pipetted into a microwell and allowed to incubate for 1 hour. After having emptied the microwell and rinsed it with 2×100 µl of PBS buffer containing 0.5% of ovalbumin and 0.1% of Tween 20 (PBS-OA-T), 100 µl of this same buffer are then added and allowed to incubate for 1 hour. The solution is then drawn off, and 35 µl of a solution of goat IgG at x ng.ml$^{-1}$ (0.5<x<1 000) diluted in a PBS buffer containing 0.1% of Tween 20 are then introduced and allowed to incubate for 40 minutes. Once the microwell has been emptied and rinsed with 2×100 µl of PBS-OA-T 100 µl of PBS-OA-T are introduced. After 30 minutes, the liquid is replaced with 35 µl of a dilute solution of anti-IgG labeled with colloidal gold (45-fold dilution of the solution marketed, in PBS-OA-T), and then incubated for 3 hours. A final rinsing cycle is carried out, washing the microwell 3 times with 200 µl of PBS-OA-T, followed by 2×100 µl of PBS. The liquid is then carefully drawn off, and the gold colloid attached to the walls of the microwell is then dissolved and detected as indicated in example 1.

Figure 6:
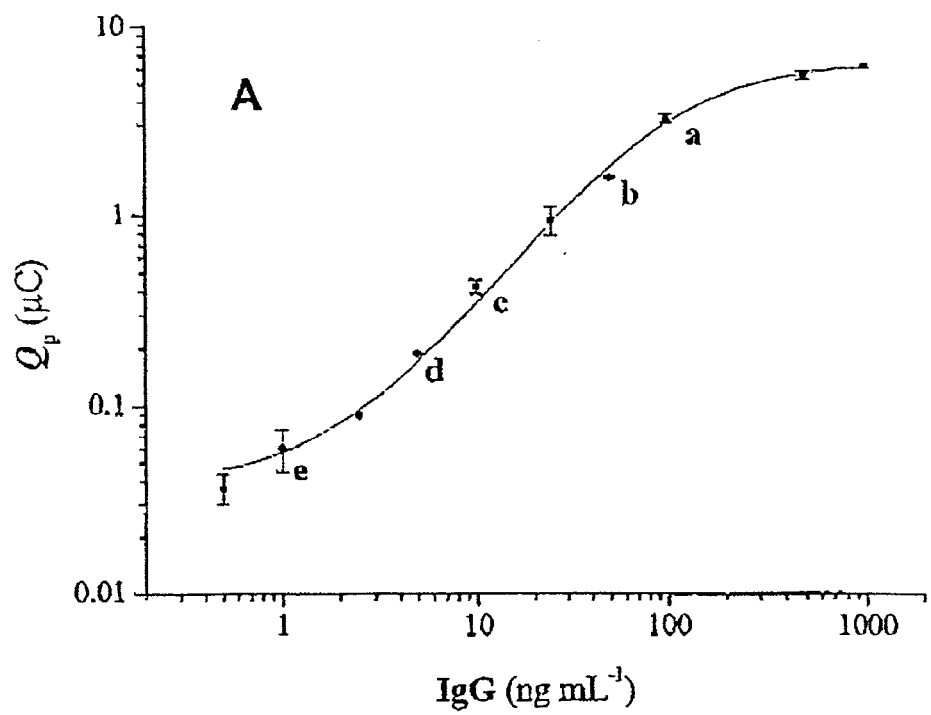
FIG. 6. (A) log-log calibration curve for the IgG noncompetitive immunoassay. (B) anodic stripping voltammetry curves obtained for various concentrations of IgG. The curves are identified by letters in order to make them correspond to the concentrations indicated by the same letters on the IgG calibration curve.
Figure 6:
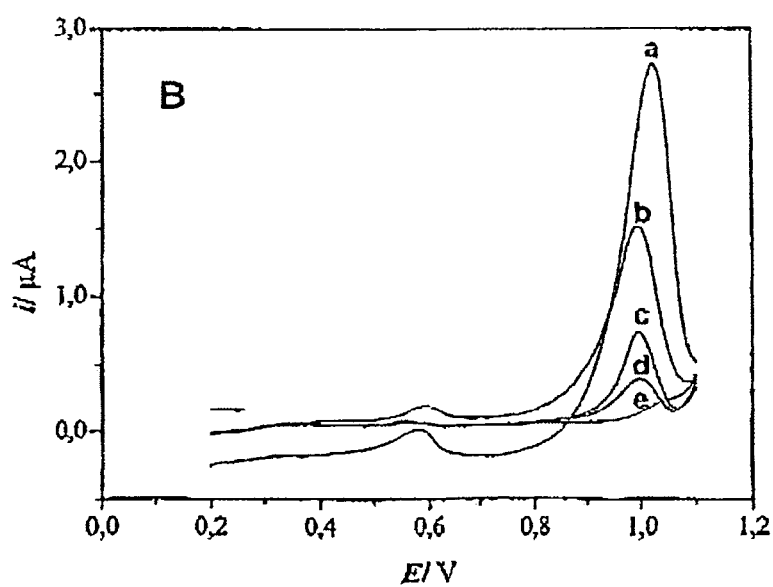
Figure 7:
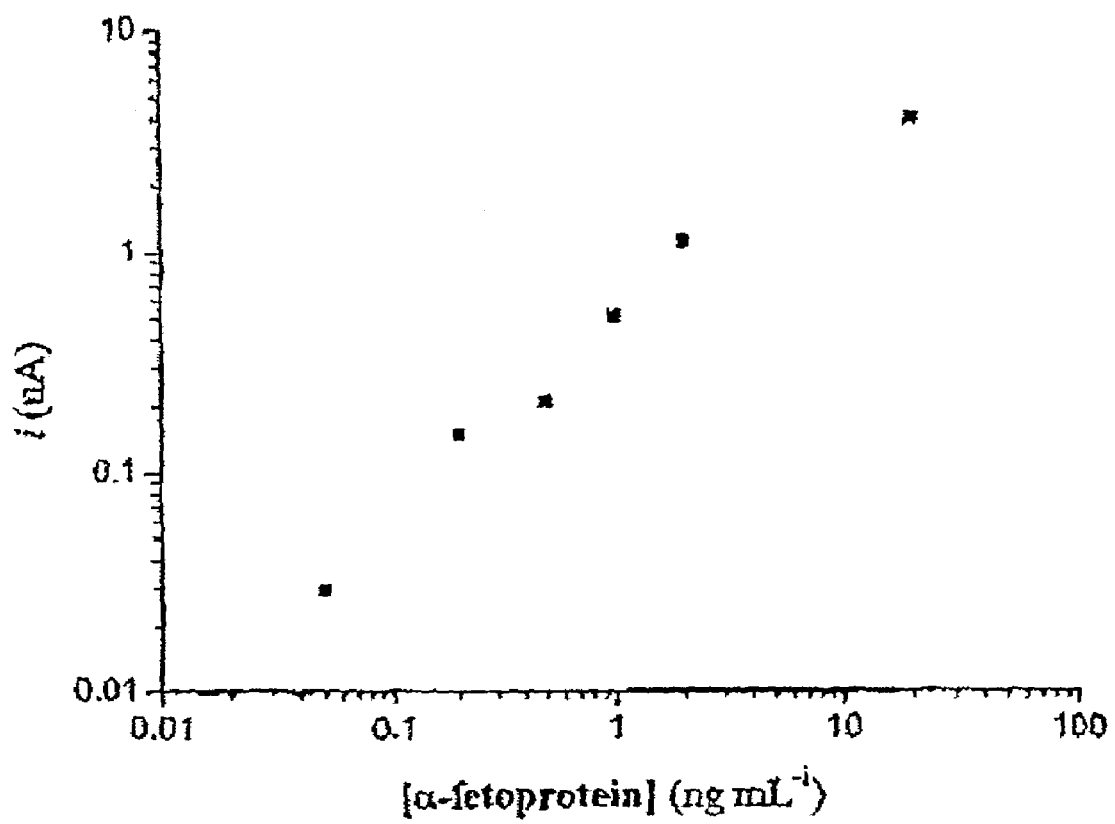
FIG. 7. Log-log calibration curve for the α-fetoprotein noncompetitive immunoassay.

Some examples of measurements obtained by linear anodic stripping voltammetry are given in FIG. 6A, while the corresponding goat-IgG calibration curve is represented in FIG. 6B. Each point represents the mean of 2 measurements and each measurement was obtained with a different electrode (single-use electrode). A concentration of approximately $3 \times 10^{-12}$ M of IgG could be determined.

Example 3

Noncompetitive Immunoassay for Human α-fetoprotein

80 µl of a solution of monoclonal anti-α-fetoprotein (mouse antibody) at 24 µg ml$^{-1}$ in a carbonate buffer (15 mM, pH 9.6) are pipetted into a microwell and allowed to incubate overnight at 4° C. After having emptied the microwell and rinsed it with 2×250 µl of PBS-OA-T buffer, 250 µl of this same buffer are then added and allowed to incubate for 40 min. The solution is then drawn off, and 80 µl of a solution of α-fetoprotein at x ng.ml$^{-1}$ (0.05<x<20) diluted in a PBS buffer containing 0.1% of Tween 20 are then introduced and allowed to incubate for 2 hours. Once the microwell has been emptied and rinsed with 2×250 µl of PBS-OA-T, 250 µl of PBS-OA-T are introduced. After 30 minutes, the liquid is replaced with 80 µl of a dilute solution of polyclonal antip-α-fetoprotein (goat antibody) diluted to 5 µl ml$^{-1}$ in PBS-OA-T, and incubated for 1 hour. Then, after rinsing with 2×250 µl of PBS-OA-T buffer, 50 µl of a solution of anti-goat IgG labeled with colloidal gold (45-fold dilution of the solution marketed, in PBS-OA-T) [lacuna], and then incubated for 1 h 30 min. A final rinsing cycle is carried out, washing the microwell 3 times with 250 µl of PBS-OA-T, followed by 2×250 µl of PBS-T, then 2×250 µl of PBS. The liquid is then carefully drawn off, then the gold colloid attached to the walls of the microwell is then dissolved and detected with strip microelectrodes in the following way: 50 µl of a solution of 0.1 mM Br$_2$ in 0.1 M HBr are added to the microwells for 30 min; then 40 µl are transferred into new microwells containing 10 µl of a solution of 3-phenoxypropionic acid at $2 \times 10^{-3}$ M in 0.1 N HBr. Detection of the dissolved gold is then carried out as indicated in example 1.

Production of Screen-Printed Strip Microelectrodes:

The carbon-based ink used to produce the strip microelectrodes is a commercial ink produced by Acheson Colloid (Minico® inks of the M3000-1RS series or Electrodag® inks such as 423 SS or PF 407A). The ink is screen-printed onto a rigid or semi-rigid support, preferably made of semicrystalline polystyrene or high-impact polystyrene (plates possibly between 0.1 and 2 mm thick). The fineness of the screen-printing mask obtained on a taut screen mounted on a frame, and also the nature and the mesh size of the screen, condition to a large extent the quality of the ink deposit and also its thickness. In the present invention, ink thicknesses of between 5 and 50 µm could be obtained using screen-printing frames comprising 77 or 120 threads/cm.

Figure 1:
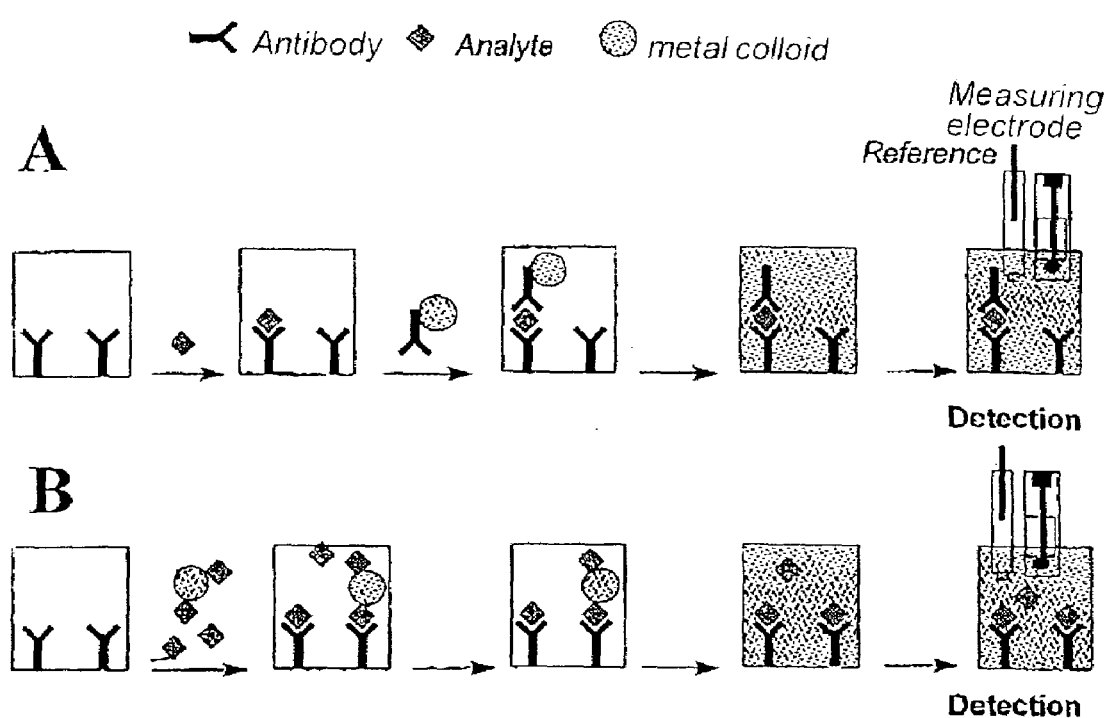
FIG. 1. Diagrammatic representation of the principle of the invention illustrated in the case (A) of a noncompetitive immunoassay and (B) a competitive immunoassay.
Figure 2:
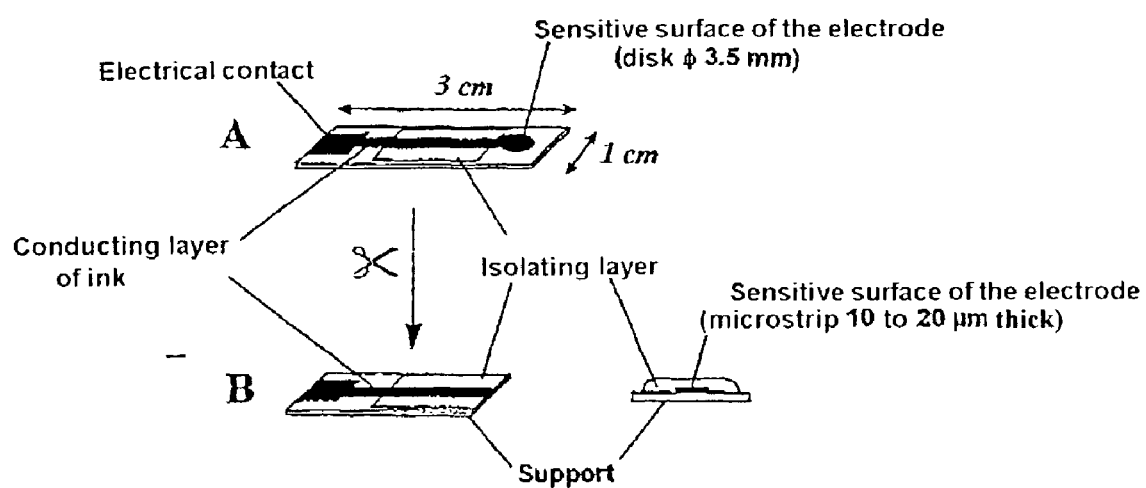
FIG. 2. Diagrammatic representation of a screen-printed disk electrode (A) and microstrip electrode (B).
Figure 3:
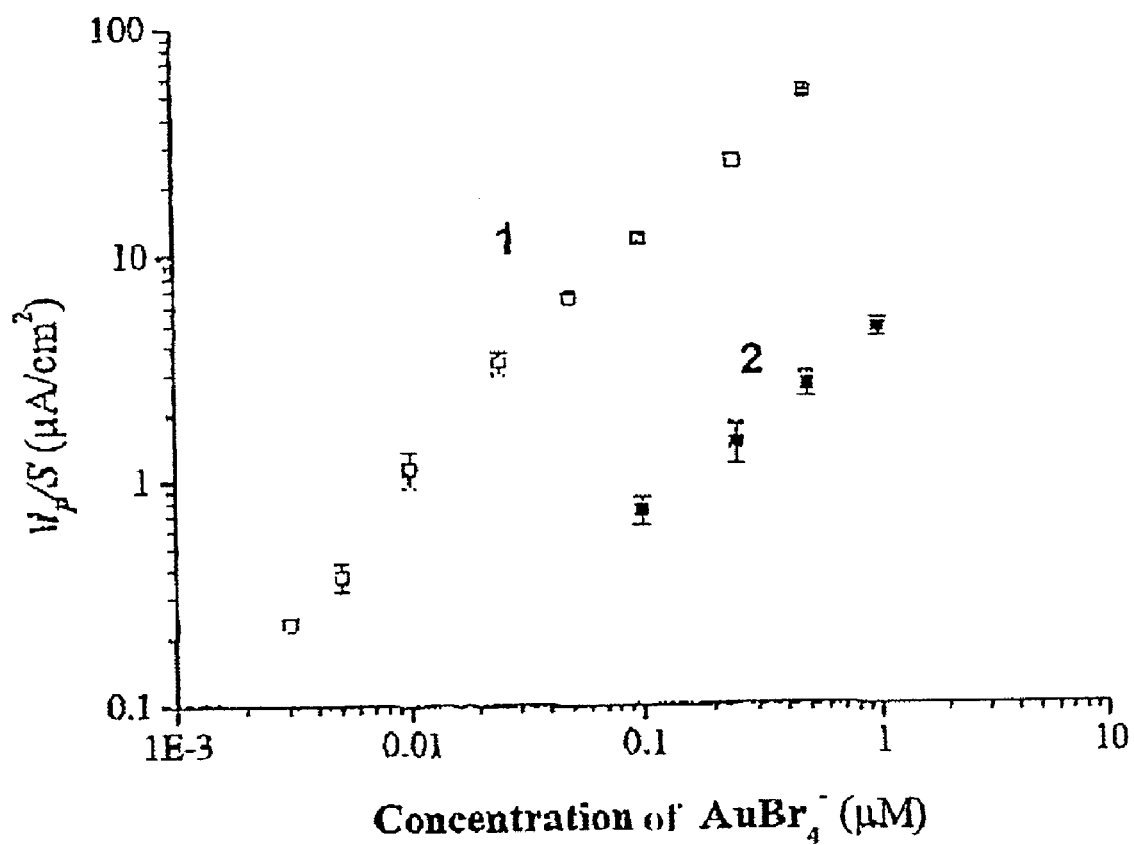
FIG. 3. Calibration curves for ionic gold, obtained (1) with a strip microelectrode and (2) with a disk electrode.

Once the ink has been screen-printed, it is left to dry in an oven at between 60 and 100° C. Next, a polystyrene-based isolating layer is deposited or screen-printed in such a way as to re-cover part of the carbon ink previously screen-printed (FIG. 2). After drying, the electrode thus constituted is cut up transversely along its thickness so as to reveal on the section a strip of carbon of micrometric thickness (depending on the thickness of carbon ink initially screen-printed) and of millimetric length (depending on the length of the motif of the electrode initially selected) (FIG. 2B).

The invention claimed is:

1. A method for the electrochemical detection or quantification of a biological substance originally coupled to colloidal metal particles, said method comprising:
    (1a) coupling a biological substance to colloidal metal particles and contacting a solid phase with a solution of the coupled material to capture the colloidal metal particles from the coupled material onto the solid phase; or
    (1b) capturing a biological substance onto a solid phase and adding colloidal metal particles, in solution, to couple with said biological substance and to capture the colloidal metal particles from the coupled material onto the solid phase;
    (2) washing the colloidal particles captured onto the solid phase;
    (3) dissolving said colloidal metal particles in a solution of a reagent able to dissolve said metal particles, to afford a solution of the metal in ionic state;
    (4) contacting the resultant solution with an electrode and electrodepositing the metal thereon by reduction and/or precipitation; and
    (5) detecting or quantifying the amount of metal deposited on said electrode to determine therefrom the amount of biological substance originally coupled to the colloidal metal particles.

2. The method as claimed in claim 1, wherein the dissolving of the colloidal metal particles is carded out in an acidic medium containing an oxidant.

3. The method as claimed in claim 2, wherein the acidic medium containing an oxidant is a solution of hydrobromic acid containing bromine, hypobromous acid or a mixture of these two compounds.

4. The method as claimed in claim 1, wherein the step of dissolving the colloidal metal particles is followed by an additional treatment intended to eliminate the product including the dissolution.

5. The method as claimed in claim 1, wherein a reagent capable of complexing the metal ions is added in solution.

6. The method as claimed in claim 1, wherein the reduction and/or precipitation of the metal on the electrode is carded out using a suitable negative potential.

7. The method as claimed in claim 1, wherein the amount of metal precipitated at the surface of the electrode is measured by variation of the potential of said electrode and analysis of the voltammetric peak which appears after reoxidation of said metal and redissolving thereof.

8. The method as claimed in claim 1, wherein the colloidal particles are selected from the group consisting of particles comprising metal and metal compounds.

9. The method as claimed in claim 8, wherein the colloidal particles are gold.

10. The method as claimed in claim 1, wherein the colloidal particles are each between 1 and 200 nm in size.

11. The method as claimed in claim 1, wherein the electrode used is a screen-printed electrode.

12. The method as claimed in claim 1, wherein the surface of the electrode is treated electrochemically or chemically in order to improve the sensitivity of detection of the dissolved metal.

13. The method as claimed in claim 1, wherein the colloidal particles dissolved in step (3) are present in a solution after coupling with the biological substance and are concentrated before dissolution.

14. The method as claimed in claim 1, wherein the biological substance coupled to the colloidal particles are selected from the group consisting of antibodies, protein receptors, antigens, haptens, proteins, peptides, oligonucleotides, and nucleic acid fragments.

15. The method according to claim 1, wherein the solid phase is the bottom of a microcuvette, the surface of a microbead, the surface of a membrane or the surface of the electrode.

* * * * *